United States Patent
Churovich (10) Patent No.: US 11,366,305 B2
(45) Date of Patent: Jun. 21, 2022

(54) ELECTRONIC VISUAL FOOD PROBE

(71) Applicant: Douglas D. Churovich, Des Peres, MO (US)

(72) Inventor: Douglas D. Churovich, Des Peres, MO (US)

(*) Notice: Subject to any disclaimer, the term of this patent is extended or adjusted under 35 U.S.C. 154(b) by 0 days.

(21) Appl. No.: 17/222,585

(22) Filed: Apr. 5, 2021

(65) Prior Publication Data

US 2021/0286163 A1  Sep. 16, 2021

Related U.S. Application Data

(63) Continuation-in-part of application No. 15/592,476, filed on May 11, 2017, now Pat. No. 10,969,572.

(60) Provisional application No. 62/334,794, filed on May 11, 2016.

(51) Int. Cl.
*G02B 23/24* (2006.01)
*G01N 33/02* (2006.01)

(52) U.S. Cl.
CPC ......... *G02B 23/2492* (2013.01); *G01N 33/02* (2013.01); *G02B 23/2423* (2013.01); *G02B 23/2484* (2013.01)

(58) Field of Classification Search
None
See application file for complete search history.

(56) References Cited

U.S. PATENT DOCUMENTS

| | | | | |
|---|---|---|---|---|
| 6,587,575 B1* | 7/2003 | Windham | ............... | A22B 5/007 382/110 |
| 7,571,675 B1* | 8/2009 | Cappadona | ........... | A47J 45/068 220/573.1 |
| 10,359,381 B2* | 7/2019 | Lewis | ..................... | G01N 33/12 |
| 2004/0136569 A1* | 7/2004 | Daley | ...................... | G06K 9/00 382/110 |
| 2010/0237850 A1* | 9/2010 | Salem Al-Ghamdi | ....................... | G01N 33/12 324/72 |
| 2012/0039356 A1* | 2/2012 | Adams | ................... | G01K 13/00 374/155 |
| 2012/0237644 A1* | 9/2012 | Luckhardt | .............. | G01N 33/12 324/693 |
| 2013/0296885 A1* | 11/2013 | Desai | .................. | A61B 17/3417 606/130 |
| 2016/0140870 A1* | 5/2016 | Connor | .............. | G09B 19/0092 356/51 |
| 2017/0221296 A1* | 8/2017 | Jain | ...................... | G07F 17/0064 |
| 2018/0324908 A1* | 11/2018 | Denker | .................. | G06V 10/40 |
| 2020/0156563 A1* | 5/2020 | Reinhart | ................... | B60P 3/14 |

(Continued)

*Primary Examiner* — Talha M Nawaz
(74) *Attorney, Agent, or Firm* — Douglas D. Churovich, Esq.

(57) ABSTRACT

An electronic visual food probe for viewing the interior of a body of food being cooked. The probe has a food-safe, heat resistant and elongated stem designed for insertion into the body of food. A thermally insulated cavity formed in one end of the stem has an opening that allows light into and out of the cavity. A light source illuminates the interior of the food exposed to the opening. An electronic image sensor receives the light reflected from the interior surfaces of the food proximate the opening and generates an elongated color image of the reflected light. An electronic display system receives the elongated color image from the image sensor and displays it on an electronic display for viewing.

7 Claims, 8 Drawing Sheets

(56) References Cited

U.S. PATENT DOCUMENTS

2021/0366206 A1\* 11/2021 Little .................... G06T 19/20

\* cited by examiner

ELECTRONIC VISUAL FOOD PROBE

CROSS REFERENCE TO RELATED APPLICATIONS

This application is a continuation-in-part of U.S. Application Ser. No. 15/592,476 filed on May 11, 2017, which is related to and claims priority from U.S. App. No. 62/334,794 filed May 11, 2016, both of which are incorporated herein by reference.

STATEMENT REGARDING FEDERALLY SPONSORED RESEARCH OR DEVELOPMENT

Not applicable.

BACKGROUND OF THE INVENTION

This invention relates generally to an electronic apparatus to facilitate the viewing of a sliver or length of a portion of food such as, for example, the visual sampling of the interior of a piece of cooked meat, and more particularly to a novel electronic probe that generates a substantially accurate visual image of the coloration of an interior sliver or length within a piece of cooked meat in a single scan for determination of sufficient level of cooking.

It is often desirable when cooking or grilling foods, and in particular when grilling meats, to determine whether the meat has been cooked sufficiently in the interior or body of the meat being cooked. One well-recognized method to determine the extent to which the interior or body of a piece of meat has been cooked is to measure or monitor the internal temperature of the item. This may entail a simple temperature measurement at a single location in the body of the piece of meat, or may be more complex, such as for example obtaining multiple temperature measurements and/or monitoring at one or multiple locations in the body of the piece of meat and/or at various depths in the body or interior of the piece of meat. It is also often desirable to determine the interior temperatures while the meat is still being cooked. That is, it is often desirable to be able to measure the meat's interior temperature without removing the food meat from its cooking environment, such as an oven or grill.

Not surprisingly, a wide variety of devices exist in the art that can determine the temperature of a piece of cooked meat. These devices may comprise a single or multiple temperature probes coupled with analog or digital readouts or displays, and may operate on mechanical or electronic principles, and can incorporate other various features such as for example, a separate probe and temperature display, rechargeable batteries, an elongated handle or grip, or a backlight display. However, temperature probes do not provide the ability to visually scan the interior of the cooked piece of meat.

Often, in addition to determining the interior temperature of a cooked piece of meat, it is desirable to examine the coloration of the interior of the meat to more accurately ascertain the distribution of the degree of cooking the piece of meat has attained. This has traditionally been accomplished by slicing into the meat while still in the cooking environment with a knife or other utensil to open the meat's interior for a visual inspection, or first removing the piece of meat from the cooking environment and then slicing into the meat with a knife or other utensil to open the meat's interior to view. Of course, cutting and viewing the meat while still in its cooking environment is difficult and uncomfortable at the least, and potentially dangerous at the worst in exposing the person cooking the meat to extremely high heat, seared heated metal, and open flames. In addition, this traditional technique has the undesirable result of marring the meat prior to presentation and consumption. Further, whether in the cooking environment or after being removed from the cooking environment, slicing or cutting the meat exposes those portions of the meat to the low temperature environment prematurely, which results in discoloration and less appeal, and can lead to the determination that additional cuts or slices or cooking may be warranted.

It would therefore be desirable to have a device or apparatus that can readily and accurately discern and display the coloration of the interior of a cooked or cooking piece of meat (or a body of some food type other than meat) without requiring that the meat (or a body of some food type other than meat) be sliced open for visual inspection. In addition, it would be further desirable for such a device to be able to quickly and accurately discern and display the coloration of the interior of a cooked or cooking piece of meat (or a body of some food type other than meat) without removing the meat (or a body of some food type other than meat) from the cooking environment. As will become evident in this disclosure, the present invention provides such benefits over the existing art.

BRIEF DESCRIPTION OF THE DRAWINGS

The illustrative embodiments of the present invention are shown in the following drawings which form a part of the specification.

DETAILED DESCRIPTION

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
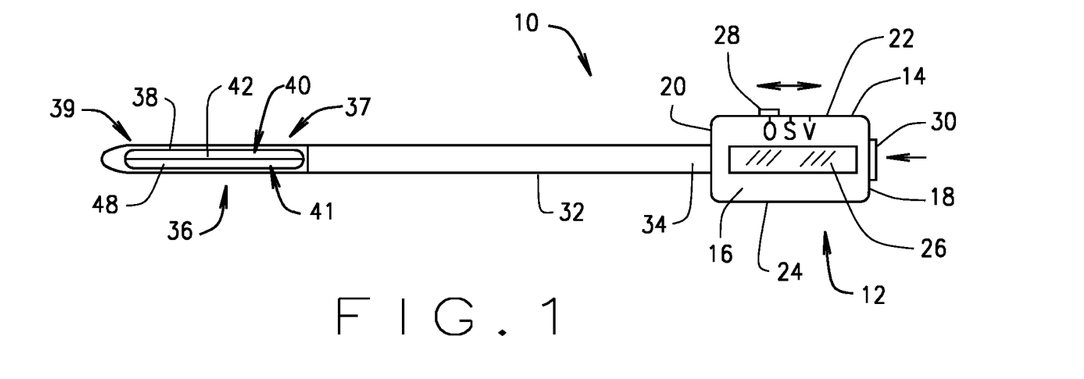
FIG. 1 is a top view of a first representative embodiment of an electronic visual food probe incorporating features of the present invention.
Figure 2:
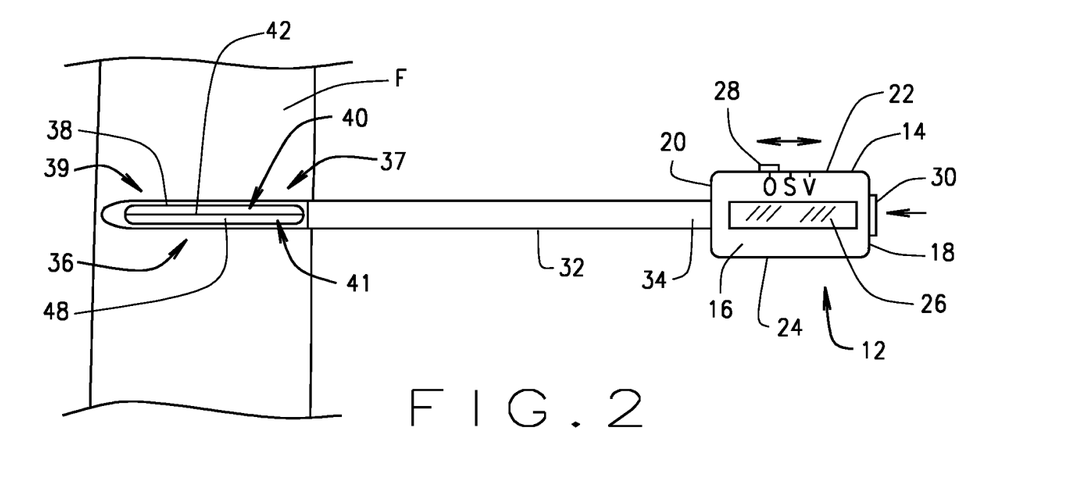
FIG. 2 is the top view of the first representative embodiment of FIG. 1, with the stem of the probe partially inserted into a piece of meat.

In referring to the drawings, a first representative embodiment of the novel electronic visual food probe 10 of the present invention is shown generally in FIG. 1, where the present invention is depicted by way of example, and in FIG. 2, where the present invention is depicted by way of example inserted into a body of food F. In this first representative embodiment, the food probe 10 comprises an electronic display system 12 contained in a slightly flattened box-shaped handle 14, having dimensions of approximately one inch wide by two inches long by ½ inch deep. The handle 14 has a generally rectangular face 16, a first end 18, a second end 20 parallel to and opposite the first end 18, a first side 22 and a second side 24 parallel to and opposite the first side 22. A flat digital color display 26 is positioned generally in the center of the outer surface of face 16 of the handle 14. A three-position mode switch 28 is positioned on the first side 22 of the handle 14, and an activation button switch 30 is positioned on the first end 18 of the handle 14. Of course, the configuration, shape and dimensions of the handle 14 are not limited to these particular specifications, but can vary substantially for a variety of reasons, including without limitation, aesthetic considerations, ability to house various shapes and sizes of components in the handle 14.

Figure 8:
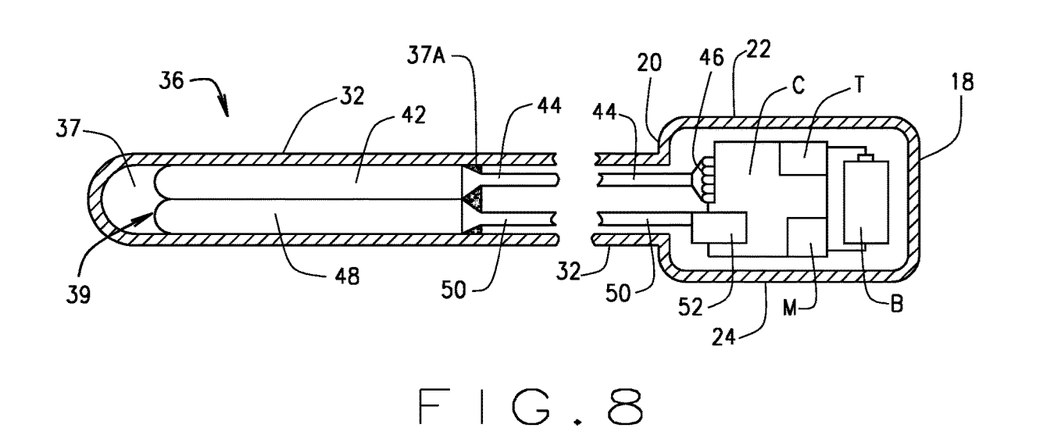
FIG. 8 is a split cut-away top view of the first representative embodiment of the electronic visual food probe of FIG. 1.

An elongated, rigid, substantially uniform tubular stem 32, having a proximal end 34 and a distal end 36, the stem 32 extends at its proximal end 34 from the second end 20 of the handle 14, where the stem 32 is rigidly attached to the handle 14. From its distal end 36 to its interface with the electronic display system 12, the stem 32 defines an inner cavity 37. A seal 37A (FIG. 8) seals the upper end of the cavity 37 inside the stem 32 proximate the interface between a pair of optical elements, optical lenses 42 and 48, and their respective fiber optic cables 44 and 50, in order to prevent the intrusion of moisture, food components or other such undesirable material, such that the cavity 37 and stem 32 form a housing 39 for the optical lenses 42 and 48. The seal 37A is formed of a solidified liquid sealant material injected into the area above the optical lenses 42 and 48. Of course, the cavity 37 can be filled with one or more materials and fixtures to positionally secure various components within the cavity 37, including for example, various adhesives, tapes, and mounting brackets. Alternately, the cavity 37 and the housing 39 can be part of a separate component that can be attached to the stem 32 (not shown). Referring again to FIGS. 1 and 2, the stem 32 is approximately eight inches long, has an outer diameter of preferably less than one-fourth inch, has a generally straight, longitudinal opening along the stem 32 near the distal end 36 that is filled and sealed by a rigid window 38 that is generally translucent or transparent to visible light. The window 38 has a width of approximately one fourth the circumference of the stem 32, and extends from a position near the tip 33 of the distal end 36 of the stem 32 approximately two inches toward the proximal end 34. The window 38 will have a length of at least one-half inch. The portion or length of the stem 32 having the window 38 may be referred to as the imaging section of the probe 10.

The stem 32 encases two optical or light transmitting conduits, 40 and 41. The light transmitting conduit 40 comprises a first fiber optic cable 44, which attaches at one end to a first elongated optical lens 42, and attaches at the opposite end to an optical lens 45 that collects light from a light-emitting-diode ("LED") array 46. The first optical lens 42 is secured inside the stem 32 behind the window 38 and connects to the first fiber optic cable 44. The first fiber optic cable 44 then extends up through the stem 32 and into the handle 14, where it connects to the optical lens 45 positioned adjacent the LED array 46, both being housed in the handle 14. The first optical lens 42, the first fiber optic cable 44 and the LED array 46 are interconnected and configured such that when the LED array 46 is activated, the light so generated will travel through the first fiber optic cable 44 and into the first optical lens 42. The optical lens 42 receives the LED light from the fiber optic cable 44 and redirects the light to a direction perpendicular to and away from the central axis of the tubular handle 14 and in a dispersed length such that the light generated by the LED array 46 exits the window 38 along substantially the full length of the window 38 and spreads radially outward relative to the central axis of the tubular handle 14. As can be appreciated, light generated by the LED array 46 can thereby be directed to the inner surface of a body of food F or meat adjacent the window 38 when the distal end 36 of the stem 32 is inserted in the body of food F, to create an illuminated region of the body of food F.

The light transmitting conduit 41 comprises a second fiber optic cable 50 that attaches at one end to a second elongated optical lens 48, and at the opposite end to a digital image sensor 52, where the image sensor 52 is fixedly positioned relative to the distal end 36 of the stem 32 and to the window 38. The image sensor 52 may comprise a single electronic diode, or two or more electronic image collection components such as discrete CCD's or other electronic image devices or components. The second optical lens 48 is secured inside the stem 32 behind the window 38 generally parallel to the first optical lens 42, and connects to the second fiber optic cable 50. The second fiber optic cable 50 then extends up through the stem 32 and into the handle 14, where it connects to the digital image sensor 52. The second optical lens 48, the second fiber optic cable 50 and the digital image sensor 52 are interconnected and configured such that light entering the second optical lens 48 from the window 38 in the stem 32 travels through the second optical lens 48, is directed at a right angle up and through the second fiber optic cable 50, and to the digital image sensor 52. The digital image sensor 52 collects a color image of the light from the second fiber optic cable 50 that has been reflected by a cross-section of the body of food F exposed to the window 38 (i.e., the illuminated region), and converts the image into electronic data representative of the color image of the interior of the body of food F (such as meat) thus received. The second optical lens 48 collects light from substantially the full length of the window 38. Thus, as can be understood, when the distal end 36 of the stem 32 is inserted into a body of food F (such as a cooked piece of meat) the fiber probe 10 creates a long and thin electronically displayable image of the coloration of the interior portion of that food item along the length of the window 38 in the stem 32.

Referring again to FIG. 8, a small computer processor C is housed in the handle 14 and acts as an electronic data converter to convert the images generated by the digital image sensor 52 into electronic still or video data files. The computer processor C stores these electronic files in a digital memory unit M attached to the computer processor C in the handle 14, and displays the image on the flat digital color display 26. A small replaceable battery B, housed in the handle 14, provides electronic power to operate the electronic components of the probe 10. The computer processor C, memory unit M, color display 26 and battery B, collectively comprise an electronic display system.

The three-position mode switch 28 allows a user to select between three modes: (i) OFF, which deactivates the probe 10 electronic components; (ii) PHOTO, which only allows the probe 10 to take instantaneous photo, or "still" shots of the interior of the food being probed; and (iii) VIDEO, which allows the probe 10 to act as a video camera. The button switch 30 activates the camera functions of the probe 10. That is, when the distal end 36 of the stem 32 is inserted into a body of food (such as a cooked piece of meat), and when the three-position mode switch 28 is in the PHOTO position, the probe 10 will take a "still" image of the interior of the food (such as cooked meat) along the length of the window 38 of the stem 32 when the button switch 30 is depressed as shown in FIG. 1. Similarly, when the distal end 36 of the stem 32 is inserted into a body of food (such as a cooked piece of meat), and when the three-position mode switch 28 is in the VIDEO position, the probe 10 will take a "video" image of the interior of the food (such as cooked meat) along length of the window 38 of the stem 32, starting when the button switch 30 is first depressed and stopping when the button switch 30 is depressed a second consecutive time. These images, whether still or video, are stored in the digital memory unit M and displayed on the flat digital color display 26.

As can be appreciated, the displayable images generated by the probe 10 are elongated and relatively thin strip- or sliver-shaped to correspond to the same-shaped cross-section portions of the body of food F or cooked meat adjacent the window 38. Accordingly, the displayable images will have a length substantially longer than the average width of the distal end 36 of the stem 32, typically at least one-half inch, such as for example a length that is at least twice the average width of the distal end 36 of the stem 32. Of course, the length of the displayable images may be three, four, five or even more, greater than the average width of the window 38 and/or the distal end 36 of the stem 32. Such elongated displayable images generated by the probe 10 provide a spectrum view of the cross-section of the body of food F adjacent the window 38. Hence, inserting the imaging section of the stem 32 in a generally perpendicular fashion into a one inch thick meat steak (see, e.g., FIG. 2) will allow the probe 10 to quickly generate an accurate strip- or sliver-shaped color-indicative or colored displayable image on the digital color display 26 that spans the full width of the interior of the steak. This provides the user with a quick and accurate visual check on the degree to which the steak has been cooked, or the "doneness" of the steak, and an actual representation of the color spectrum of the meat across the entire width of the steak at the point of insertion of the probe 10.

Further, it may be desirable to only display a portion of the strip-shaped color image, such as for example when only a portion of the window 38 penetrates into the body of food F and the remainder of the window 38 will reveal no portion of the cross-section of the body of food F pressed against the distal end of the probe 10. In such circumstances, the electronic display system of the probe 10 is adapted to truncate the strip- or sliver-shaped color image that is displayed on the digital color display 26 so as to only display on the electronic display 26 the cross-section of the body of food F actually pressed against the distal end of the probe 10. This can be accomplished in various ways well known to those of skill in the art. For example, in one embodiment, computer code instructs the computer processor C to identify digital pixels in the strip- or sliver-shaped color image that do not correspond in color to the food F being probed (such as for example a bright yellow or a black), and eliminate those pixels from the image being displayed. In another embodiment, a mechanical sensor (not shown) can be mounted proximate the window 38 that determines the depth the probe 10 penetrates the body of food F, communicates that information to the computer processor C, and the computer code instructs the computer processor C to truncate that portion of the strip- or sliver-shaped color image that is calculated to be outside the body of food F. Other such various techniques, known to those skilled in the art, can alternatively be implemented.

Preferably, the entire probe 10 is constructed of materials that are physically rugged, food-safe (usable for contact with food products and goods without causing harm to the food or the consumer of the food), and can withstand the heat from cooking environments, up to and including the heat generated by open flames, such as for example a fire pit or BBQ grill, such that the food probe 10 can function properly and safely in such environments and under such conditions. However, the probe 10 can be constructed such that just the stem 32 and the window 38 comprise materials that are physically rugged, food-safe, and can thermally insulate the cavity 37 from the heat generated by cooking, including the heat generated by open cooking flames, such as those generated in a barbeque grill, fire pit, oven or stove. Such temperatures may for example be as low as 200 degrees Fahrenheit, or may be higher, including various temperatures across the range of 200 degrees Fahrenheit to 600 degrees Fahrenheit, or even higher. The term "food-safe" meaning that the material can be used in conjunction with the preparation and serving of food items for human consumption.

Figure 3:
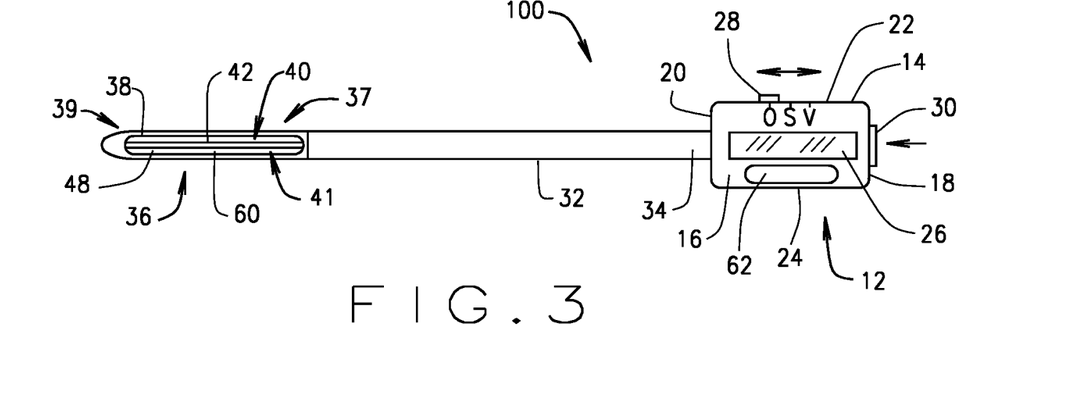
FIG. 3 is a top view a second representative embodiment of an electronic visual food probe incorporating features of the present invention.

A second embodiment 100 of the present invention is shown in FIG. 3.

In the embodiment of the probe 100, a temperature sensor 60 is positioned in the stem 32 next to the second optical lens 48 in the vicinity of the window 38. The temperature sensor 60 measures the temperature of the body of food F in proximity to the window 38 and generates an electronic signal indicative of the temperature so measured. The temperature sensor 60 is connected by wire through the stem 32 and into the electronic display system 12 to connect to the computer processor C. The computer processor C receives the electronic signal from the temperature sensor 60, converts the signal into an electronic display signal indicative of the temperature measured by the sensor 60, and generates a display on a second LCD display 62 as readable characters in degrees Fahrenheit and Centigrade indicative of the temperature measured by the temperature sensor 60. Of course, alternatively, the temperature and the digital image of the cross-section of the body of food F can both be displayed on a single electronic display.

Figure 4:
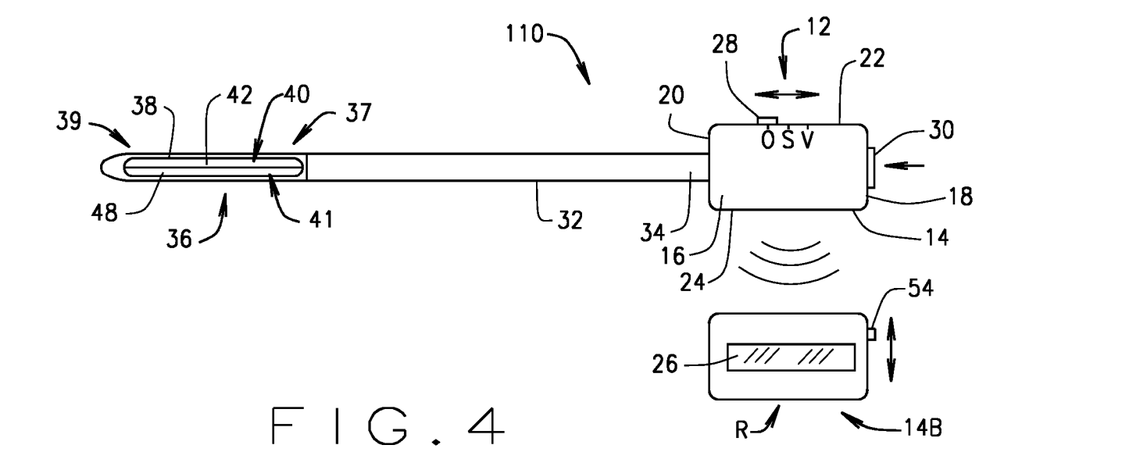
FIG. 4 is a top view a third representative embodiment of an electronic visual food probe incorporating features of the present invention.

A third embodiment 110 of the present invention is shown in FIG. 4, where the digital color display 26 is separated from the handle 14 and positioned in a housing component 14B. The handle 14 connects to the stem 32 and houses the computer processor C and memory unit M. In addition, an electronic wireless transmitter T housed in the handle 14

(see FIG. 8) transmits the electronic data indicative of the color image generated by the image sensor 52 from the memory unit M or alternately the computer processor C to an electronic wireless receiver R in the housing component 14B. The wireless receiver R then communicates the electronic data to the flat digital color display 26, where the displayable image is displayed. A slidable ON/OFF switch 54 activates and deactivates the digital color display 26 of the housing component 14B.

Figure 5:
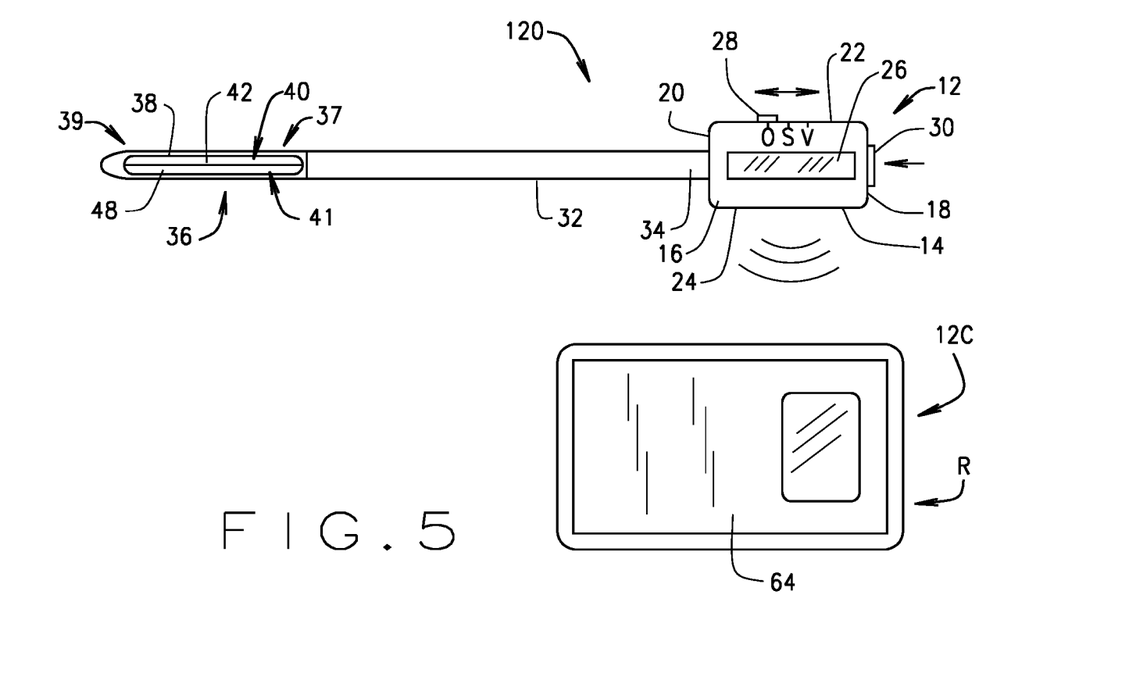
FIG. 5 is a top view a fourth representative embodiment of an electronic visual food probe incorporating features of the present invention.

A fourth embodiment 120 of the present invention is shown in FIG. 5, in which the handle 14 of the probe 120 communicates with a personal data device 12C, such as for example a personal computer, a laptop computer or tablet device, a cellular telephone, a "Bluetooth" capable device or electronic component, or other similar device having a digital display 64, to display the displayable image from the image sensor 52.

In this fourth embodiment, handle 14 connects to the stem 32 and houses the computer processor C and memory unit M. In addition, the electronic wireless transmitter T is housed in the handle 14 and transmits the electronic data indicative of the color image generated by the image sensor 52 from the memory unit M or alternately the computer processor C to an electronic wireless receiver R housed in a personal data device such as for example the cellular telephone 12C. The personal data device 12C receives the electronically captured image from the memory unit M or the computer processor C and generates the image on the digital display 64 of the device 12C. The personal data device 12C can also store or otherwise utilize or manipulate the electronic data received from the wireless transmitter T as determined by the software stored in and accessible for use on the device.

Figure 6:
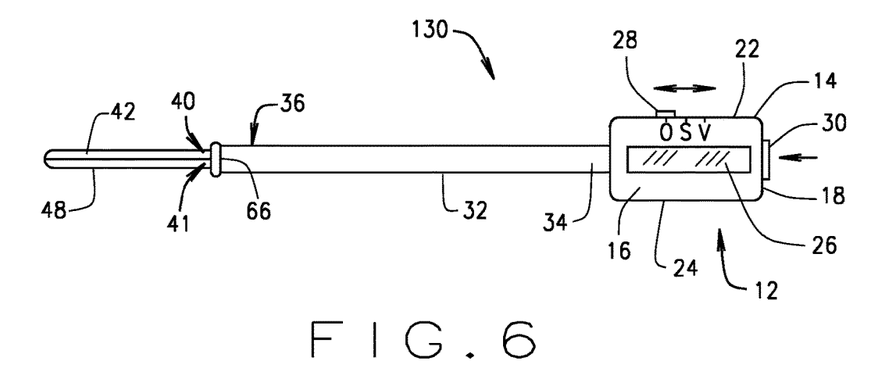
FIG. 6 is a top view a fifth representative embodiment of an electronic visual food probe incorporating features of the present invention.

A fifth embodiment 130 of the present invention is shown in FIG. 6.

Here, the stem 32 does not extend the full length of the probe 130. Rather, the light transmitting conduits 40 and 41 are rigidly attached to and extend out of the distal end 36 of the stem 32. A high temperature seal 66 at the interface between the light transmitting conduits 40, 41 and the distal end 36 of the stem 32 prevents moisture, food components or other such undesirable materials from entering the stem 32. Consequently, the light transmitting conduits 40 and 41, and their respective first and second first optical lenses 42 and 48, must be physically rugged, food-safe, and can withstand the heat generated by cooking, including the heat generated by open cooking flames, such as those generated in a barbeque grill, fire pit, oven or stove. In addition, one or more of the light transmitting conduits 40 and 41 and their respective first and second first optical lenses 42 and 48 must be substantially rigid. Further, there is no window 38 through which the first and second first optical lenses 42 and 48 must view the food being probed. Of course, the stem 32 can be solid or otherwise filled so as to eliminate the need for the seal 66.

Figure 7:
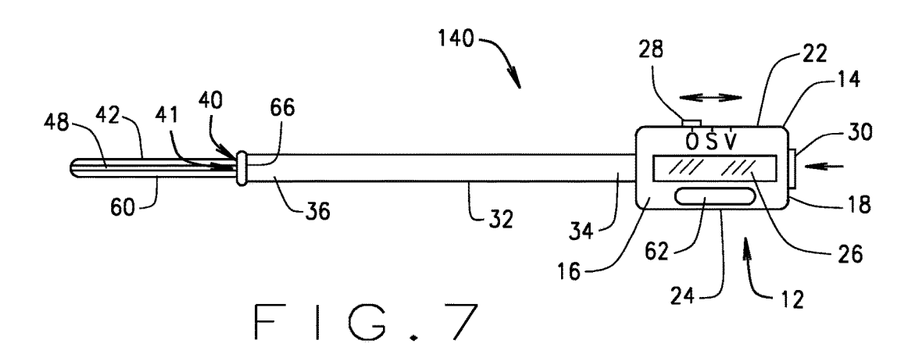
FIG. 7 is a top view a sixth representative embodiment of an electronic visual food probe incorporating features of the present invention.

A sixth embodiment 140 of the present invention is shown in FIG. 7. As in the embodiment 130 of FIG. 6, the stem 32 does not extend the full length of the probe 140. Rather, the light transmitting conduits 40 and 41 are rigidly attached to and extend out of the distal end 36 of the stem 32. Yet, in addition, the temperature probe 60 of embodiment 100 of FIG. 3, is also rigidly attached to and extends out of the distal end 36 of the stem 32. The high temperature seal 66 at the interface between the light transmitting conduits 40 and 41 and the temperature probe 60, and the distal end 36 of the stem 32 prevents moisture, food components or other such undesirable materials from entering the stem 32. Consequently, the light transmitting conduits 40 and 41 and their respective first and second first optical lenses 42 and 48, and the temperature probe 60, must all be physically rugged, food-safe, and can withstand the heat generated by cooking, including the heat generated by open cooking flames, such as those generated in a barbeque grill, fire pit, oven or stove. In addition, one or more of the light transmitting conduits 40 and 41, the first and second first optical lenses 42 and 48, and the temperature probe 60, must be substantially rigid. Again, there is no window 38 through which the first and second first optical lenses 42 and 48 must view the food being probed.

Figure 9:
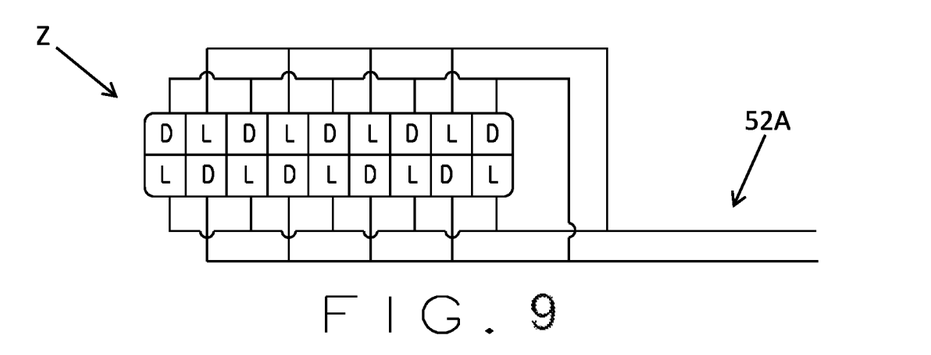
FIG. 9 is a diagram of an embodiment of an array of light sensor diodes and LED diodes for an alternate embodiment of the electronic visual food probe incorporating features of the present invention.
Figure 10:
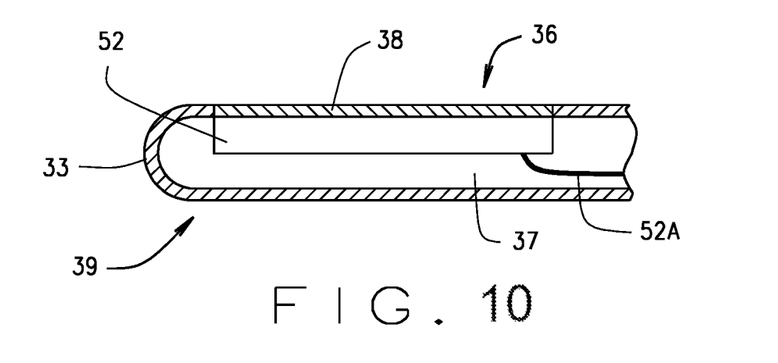
FIG. 10 is a cut-away top view of an alternate embodiment of the distal end of the stem of the electronic visual food probe incorporating features of the present invention.
Figure 11:
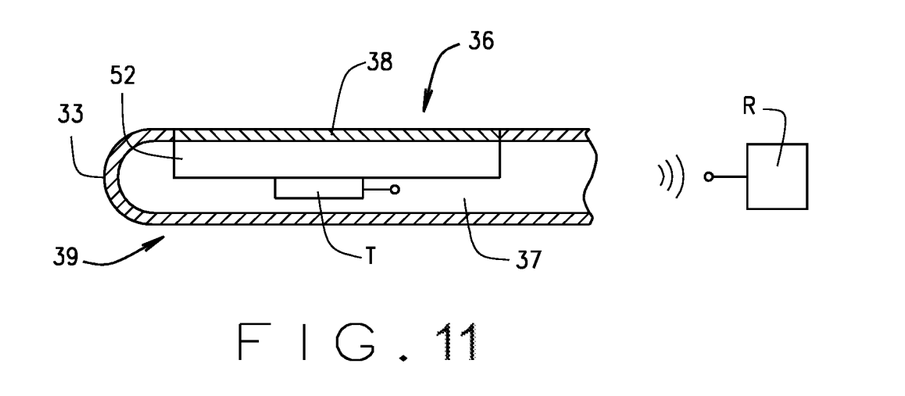
FIG. 11 is a cut-away top view of an alternate embodiment of the distal end of the stem of the electronic visual food probe, and a remote wireless receiver, incorporating features of the present invention.
Figure 12:
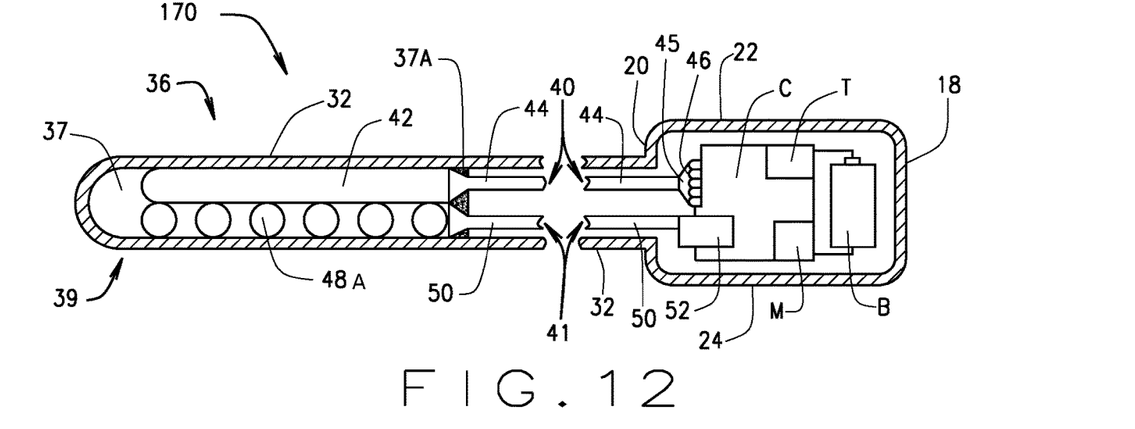
Figure 13:
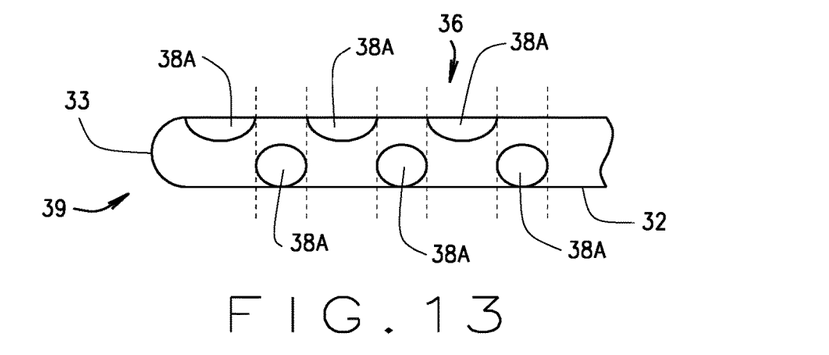
Figure 14:
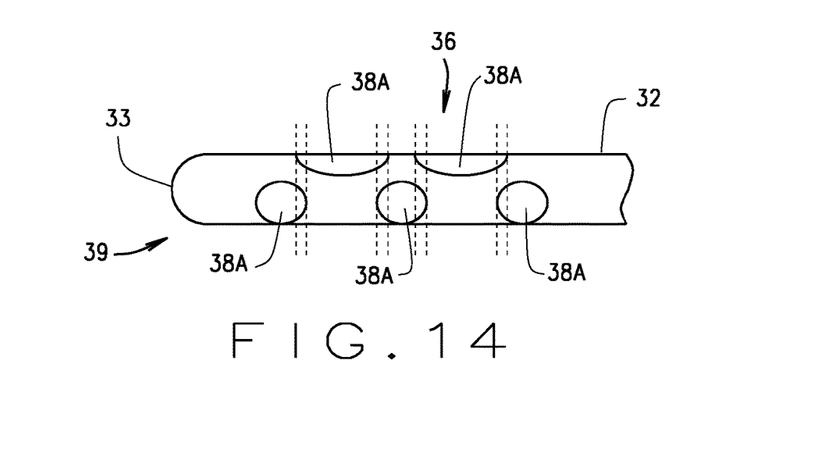
Figure 15:
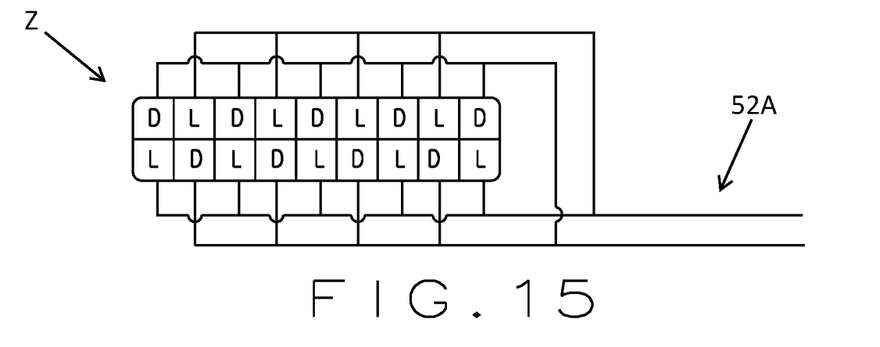
Figure 16:
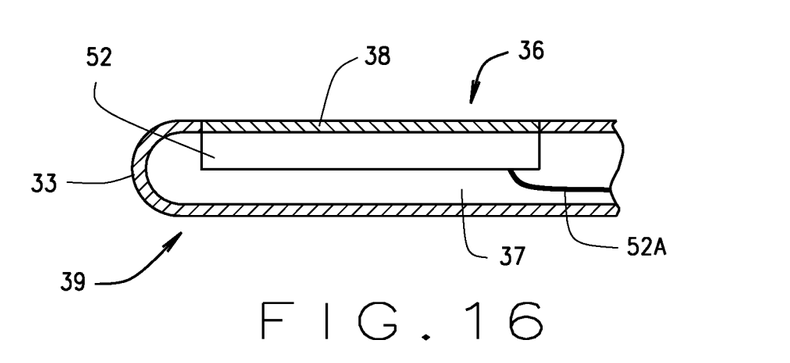

FIG. 9 depicts one example of an array Z of image sensor diodes D interlaced with a set of LED's L, where the collection of LED's L form the light source for the probe and the collection of image sensor diodes D form the image sensor 52, and both are positioned in the cavity 37 proximate the window 38 to generate the light required to create the illuminated region of the cross-section of the body of food F proximate the window 38. The electronic data is communicated to the computer processor C via wires 52A. In such configurations, no light transmitting conduit will be required. FIG. 10 depicts the positioning of the image sensor 52 proximate the window 38 in the cavity 37 in the distal end 36 of the stem 32, and the wire 52A operatively connecting the image sensor 52 to the computer processor C. FIG. 11 depicts the positioning of the image sensor 52 proximate the window 38 in the cavity 37 in the distal end 36 of the stem 32, along with a wireless transmitter T that wirelessly communicates the digital color image from the image sensor 52 to a wireless receiver R, which can be operatively associated with the computer processor C to receive the digital color image from the transmitter T and communicate the image data to the computer processor C.

While I have described in the detailed description several configurations that may be encompassed within the disclosed embodiments of this invention, numerous other alternative configurations, that would now be apparent to one of ordinary skill in the art, may be designed and constructed within the bounds of my invention as set forth in the claims. Moreover, the above-described novel mechanisms of the present invention, shown by way of example in in the various embodiments depicted in FIGS. 1-11, can be arranged in a number of other and related varieties of configurations without departing from or expanding beyond the scope of my invention as set forth in the claims, such as for example making insubstantial changes to the dimensions of the probe components.

For example, the first fiber optic cable 44 and the second fiber optic cable 50 can each be constructed of a single cable, a bundle of cables or a collection of spliced cables. Also, it is not necessary that the light source for the probe 10 be an LED array, such as at 46, but can alternately be for example a light bulb, a single LED, a laser emitter, or any of a myriad of other electronic light emitting sources. Further, the first light transmitting conduit 40 can, for example, alternately be replaced with an LED array 46 (or other electronic light source) positioned in the window 38. Similarly, the second light transmitting conduit 41 can be replaced with a system in which the electronic image sensor 52 is positioned in the window 38, and transmits the electronic images to the computer C either through a wire or set of wires, a cable, a structural network, or wirelessly.

Also, while preferable, it is not necessary for the stem 32 to be uniformly tubular or cylindrical. Rather, the stem 32 can be configured with a wide variety of cross-sectional shapes and sizes, so long as the stem 32 is capable of performing its allocated functions as described herein. Similarly, it is not necessary that the stem 32, the cavity 37 or the housing 39 extend in a straight and perpendicular fashion from the handle 14. Rather, any one or more of these components can be a myriad of various shapes and sizes, and can extend from the handle 14 in any of a variety of configurations, so long as the stem 32 and the imaging components can be inserted into the body of food F.

By way of further example, the stem 32 can be a variety of lengths, so long as the stem 32 has an imaging section that can be inserted into the food or meat. Likewise, the window 38 can be a variety of lengths, widths and shapes, so long as the window 38 provides the function of enabling the probe 10 to visually view and generate a displayable image indicative of the interior of a food item proximate the window 38 which is preferably a color image. While the probe 10 is operated by an internal battery B, any variety of appropriate power sources, such as for example a solar power array or an AC power cord, can be utilized to power the probe 10.

In addition, the digital color display 26 can be configured in any of a wide variety of shapes and sizes, so long as the digital color display 26 is capable of generating an electronically displayable image that substantially mimics or otherwise accurately indicates the coloration of the interior of the food product being probed.

Of course, the probe 10 need not operate with a computer C or a memory unit M, but can utilize other similar electronics, so long as such electronics provide the utility of enabling the probe 10 to take a color image from the interior of a body of food F and generate a replicated representative color image on a display, such as the digital color display 26.

Moreover, the light transmitting conduits 40 and 41 can comprise a wide variety of configurations. For example, the conduits may be comprised of one or more fiber optic cables, light transferring crystals, encased gases or liquids that can transmit visible light, or even a contained body of air or a vacuum—so long as such conduit is capable of sufficiently transmitting light so as to provide the functionality as required by this disclosure.

In addition, the optical lenses 42 and 48 can be a variety of differing shapes and sizes, and in particular can be longer or shorter or wider or thinner than depicted, or can be oriented differently within the cavity 37, so long as the lens 42 is capable of dispersing light from the LED array 46 through the window 38 in a manner to effectuate the function of the probe 10. Further, the optical lenses 42 and 48 can be through lenses that allow the passage of light through the body of the lens. Alternately, the lenses 42 and 48 can be replaced with a reflective surface that merely change the direction of the light, such as for example a mirrored surface that directs light from the LED array 46 through the window 38 (for the transmitting conduit 40), or that directs light reflected from the body of food F through the window 38 and upward into the fiber optic cable 50 (for the transmitting conduit 41). Of course, the LED array 46 can be attached to the fiber optic cable 44, and the image sensor 52 can be attached to the fiber optic cable 50, in a number of ways well understood in the art, including for example, optical adhesives and optical fittings. In addition, the LED array 46 and the image sensor 52 need not be positioned in the handle 14. Rather, either or both of the LED array 46 and the image sensor 52 can be positioned wholly or at least in part in the cavity 37 or in the housing 39, or alternatively anywhere along the length of the stem 32, or even outside (at least in part) the stem 32, the cavity 37 and/or the housing 39.

Additional variations or modifications to the configuration of the novel mechanism of the present invention, shown by way of example as embodiments of the probe depicted in FIGS. 1-11, may occur to those skilled in the art upon reviewing the subject matter of this invention. Such variations, if within the spirit of this disclosure, are intended to be encompassed within the scope of this invention. The description of the embodiments as set forth herein, and as shown in the drawings, is provided for illustrative purposes only and, unless otherwise expressly set forth, is not intended to limit the scope of the claims, which set forth the metes and bounds of my invention. Accordingly, all matter contained in the above description or shown in the accompanying drawings should be interpreted as illustrative and not in a limiting sense.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

What is claimed is:

1. An electronic visual food probe for insertion into an interior portion of a body of food being cooked to provide a color image of a cross-section of said interior portion proximate said probe, said food probe comprising:
   a. a substantially rigid stem, said stem having a proximal end and a distal end opposite said proximal end;
   b. a light source, said light source illuminating said cross-section of said interior portion of said body of food proximate said stem distal end to create an illuminated region of said cross-section;
   c. a first electronic image sensor, said first electronic image sensor being shaped, adapted and positioned relative to said stem distal end to collect reflected light from said illuminated region and to generate from said reflected light electronic data corresponding to a strip-shaped color image indicative of at least a one-half inch length of said cross-section of said interior portion of said body of food;
   d. an electronic display system comprising a computer processor and an electronic display, said computer processor receiving said electronic data from said electronic image sensor, converting said electronic data into an electronically displayable image indicative of said strip-shaped color image, and displaying said displayable image on said electronic display.

2. The electronic visual food probe of claim 1, wherein said first electronic image sensor is fixedly positioned relative to said stem distal end.

3. The electronic visual food probe of claim 1, further comprising one of: (i) a wireless transmitter and a wireless receiver; and (ii) a temperature sensor; said wireless transmitter wirelessly communicating said electronic data from said wireless transmitter to said wireless receiver, said temperature sensor positioned proximate said stem distal end, said temperature sensor sensing the temperature in proximity to said stem distal end and communicating an electronic signal indicative of the temperature sensed by said temperature sensor to said electronic display system; said electronic display system presenting information on said electronic display indicative of the temperature sensed by said temperature sensor.

4. The electronic visual food probe of claim 1, wherein said first electronic image sensor comprises two or more electronic image collection components, said two or more image collection components collecting reflected light from said illuminated region and cooperatively generating from said reflected light electronic data corresponding to said strip-shaped color image.

5. The electronic visual food probe of claim 1, wherein said stem distal end comprises an elongated inner cavity having an elongated opening, said elongated inner cavity housing at least in part said first electronic image sensor, said elongated opening extending lengthwise along the side of said stem distal end and penetrating into said elongated inner cavity, said elongated opening being at least one half inch long, said first electronic image sensor collecting reflected light from said illuminated region through said elongated opening and generating from said reflected light said strip-shaped color image.

6. The electronic visual food probe of claim 5, wherein said elongated opening has an elongated insertion portion, said elongated insertion portion comprising the length of said elongated opening inserted into said body of food, said electronic display system truncating said electronically displayable image so as to display no more of said elongated opening than said elongated insertion portion.

7. The electronic visual food probe of claim 5, further comprising a window positioned at least in part in said elongated opening, said window being at least in part either translucent or transparent to visible light.

* * * * *

UNITED STATES PATENT AND TRADEMARK OFFICE
CERTIFICATE OF CORRECTION

| | |
|---|---|
| PATENT NO. | : 11,366,305 B2 |
| APPLICATION NO. | : 17/222585 |
| DATED | : June 21, 2022 |
| INVENTOR(S) | : Douglas D. Churovich |

It is certified that error appears in the above-identified patent and that said Letters Patent is hereby corrected as shown below:

On the Title Page

Delete the title page and substitute therefore with the attached title page showing the corrected illustrative print figure.

In the Drawings

Delete drawings sheets 1-4 and substitute therefor the drawing sheets, consisting of figs. 1-11 as shown on the attached pages.

Signed and Sealed this
Twenty-ninth Day of July, 2025

Coke Morgan Stewart
*Acting Director of the United States Patent and Trademark Office*

(12) United States Patent
Churovich

(10) Patent No.: US 11,366,305 B2
(45) Date of Patent: Jun. 21, 2022

(54) ELECTRONIC VISUAL FOOD PROBE

(71) Applicant: Douglas D. Churovich, Des Peres, MO (US)

(72) Inventor: Douglas D. Churovich, Des Peres, MO (US)

( * ) Notice: Subject to any disclaimer, the term of this patent is extended or adjusted under 35 U.S.C. 154(b) by 0 days.

(21) Appl. No.: 17/222,585

(22) Filed: Apr. 5, 2021

(65) Prior Publication Data
US 2021/0286163 A1     Sep. 16, 2021

Related U.S. Application Data

(63) Continuation-in-part of application No. 15/592,476, filed on May 11, 2017, now Pat. No. 10,969,572.

(60) Provisional application No. 62/334,794, filed on May 11, 2016.

(51) Int. Cl.
*G02B 23/24*     (2006.01)
*G01N 33/02*     (2006.01)

(52) U.S. Cl.
CPC ......... *G02B 23/2492* (2013.01); *G01N 33/02* (2013.01); *G02B 23/2423* (2013.01); *G02B 23/2484* (2013.01)

(58) Field of Classification Search
None
See application file for complete search history.

(56) References Cited

U.S. PATENT DOCUMENTS

| | | | | |
|---|---|---|---|---|
| 6,587,575 | B1* | 7/2003 | Windham | A22B 5/007 382/110 |
| 7,571,675 | B1* | 8/2009 | Cappadona | A47J 45/068 220/573.1 |
| 10,359,381 | B2* | 7/2019 | Lewis | G01N 33/12 |
| 2004/0136569 | A1* | 7/2004 | Daley | G06K 9/00 382/110 |
| 2010/0237850 | A1* | 9/2010 | Salem Al-Ghamdi | G01N 33/12 324/72 |
| 2012/0039356 | A1* | 2/2012 | Adams | G01K 13/00 374/155 |
| 2012/0237644 | A1* | 9/2012 | Luckhardt | G01N 33/12 324/693 |
| 2013/0296885 | A1* | 11/2013 | Desai | A61B 17/3417 606/130 |
| 2016/0140870 | A1* | 5/2016 | Connor | G09B 19/0092 356/51 |
| 2017/0221296 | A1* | 8/2017 | Jain | G07F 17/0064 |
| 2018/0324908 | A1* | 11/2018 | Denker | G06V 10/40 |
| 2020/0156563 | A1* | 5/2020 | Reinhart | B60P 3/14 |

(Continued)

*Primary Examiner* — Talha M Nawaz
(74) *Attorney, Agent, or Firm* — Douglas D. Churovich, Esq.

(57) ABSTRACT

An electronic visual food probe for viewing the interior of a body of food being cooked. The probe has a food-safe, heat resistant and elongated stem designed for insertion into the body of food. A thermally insulated cavity formed in one end of the stem has an opening that allows light into and out of the cavity. A light source illuminates the interior of the food exposed to the opening. An electronic image sensor receives the light reflected from the interior surfaces of the food proximate the opening and generates an elongated color image of the reflected light. An electronic display system receives the elongated color image from the image sensor and displays it on an electronic display for viewing.

7 Claims, 4 Drawing Sheets

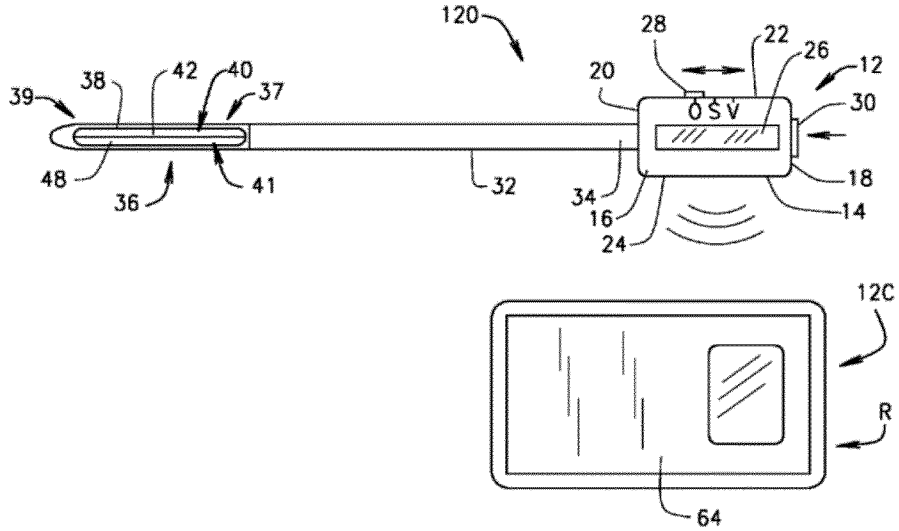

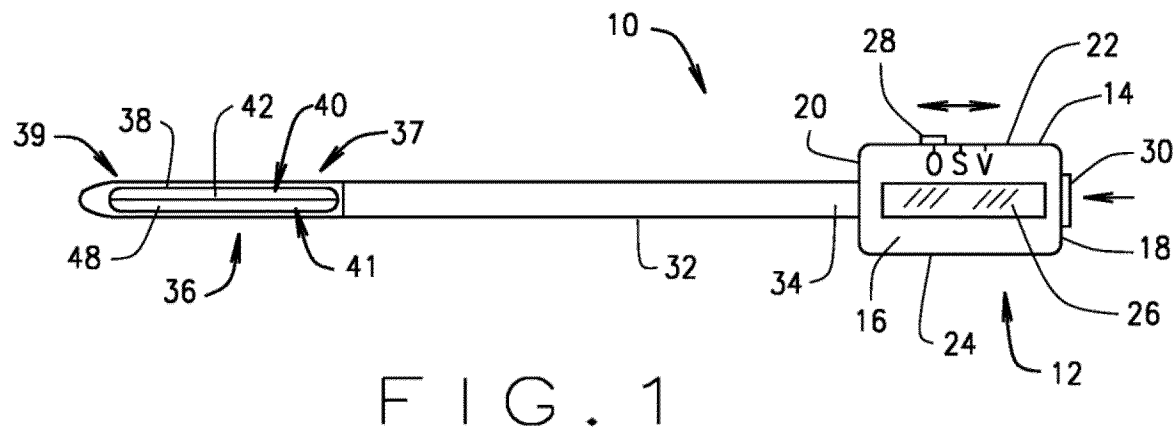
FIG. 1
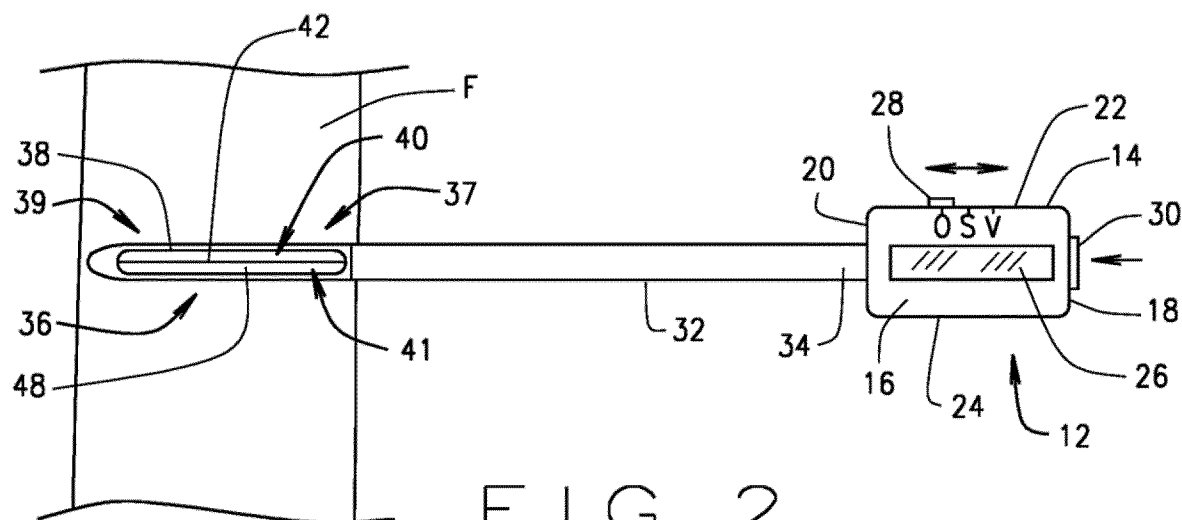
FIG. 2
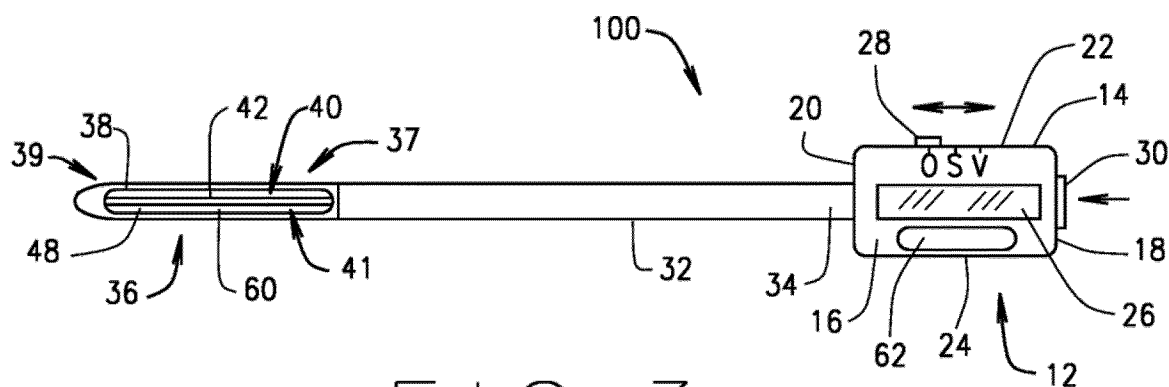
FIG. 3

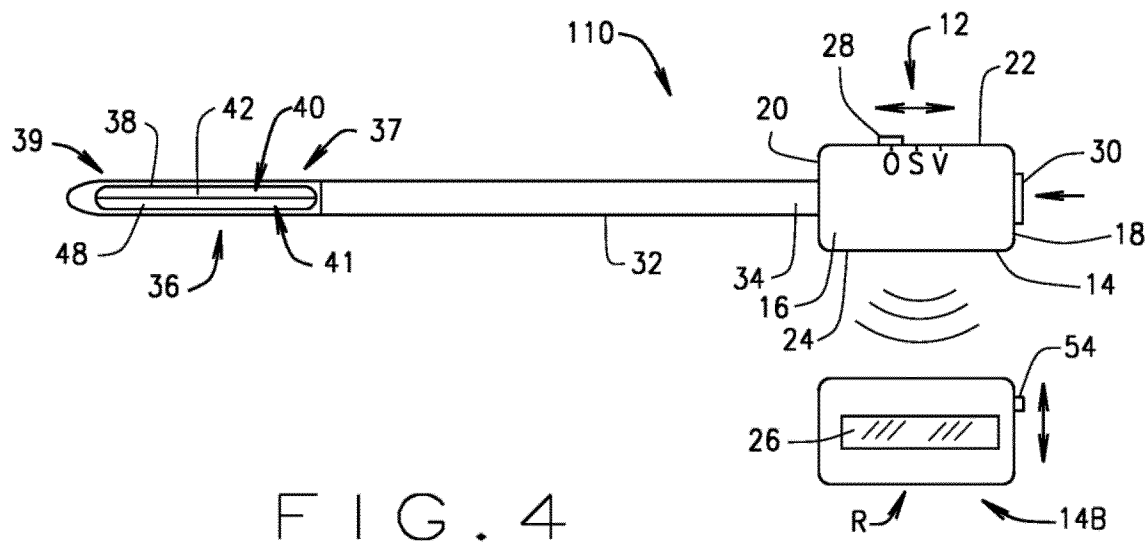
FIG. 4
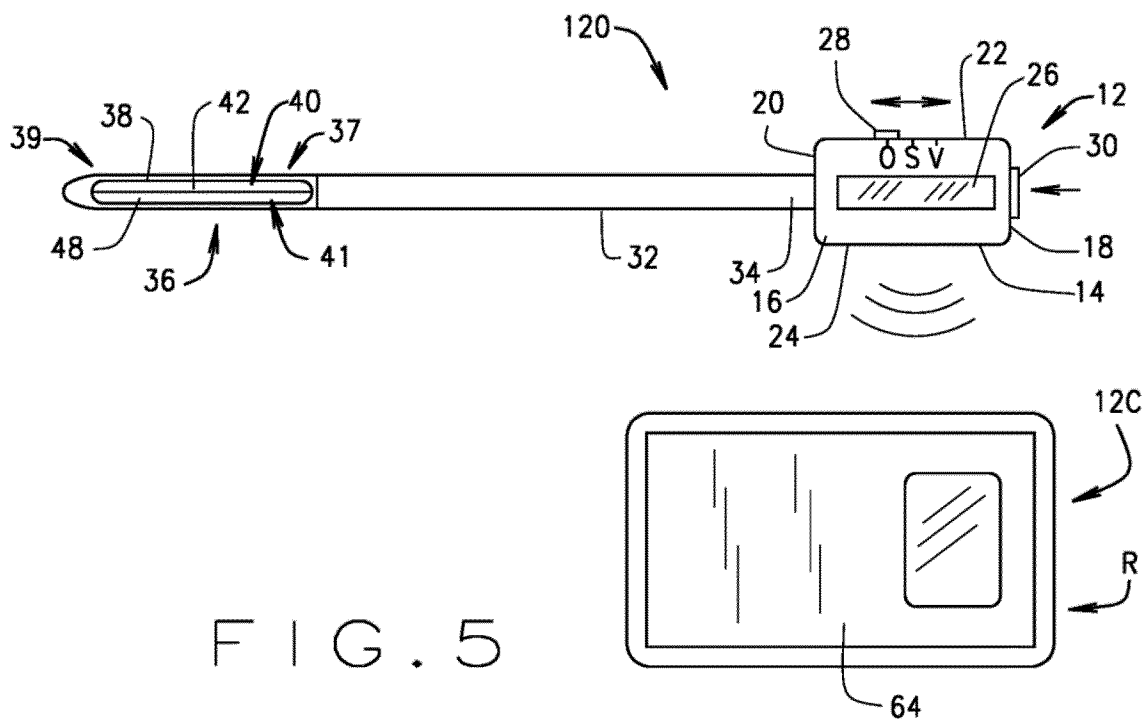
FIG. 5

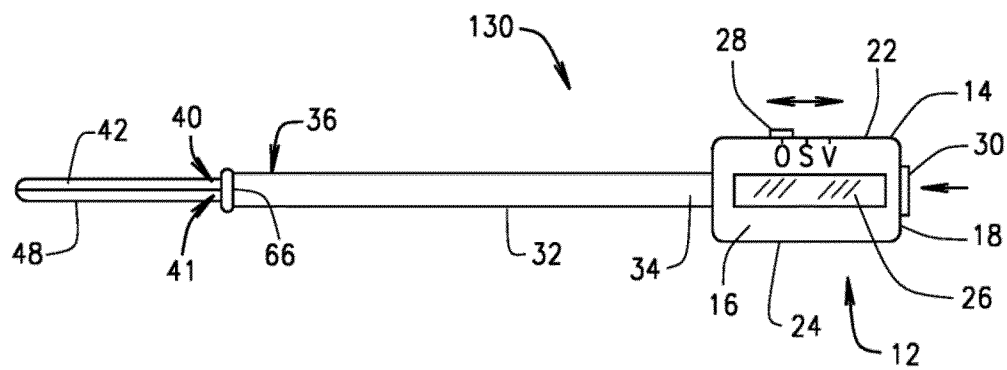
FIG. 6
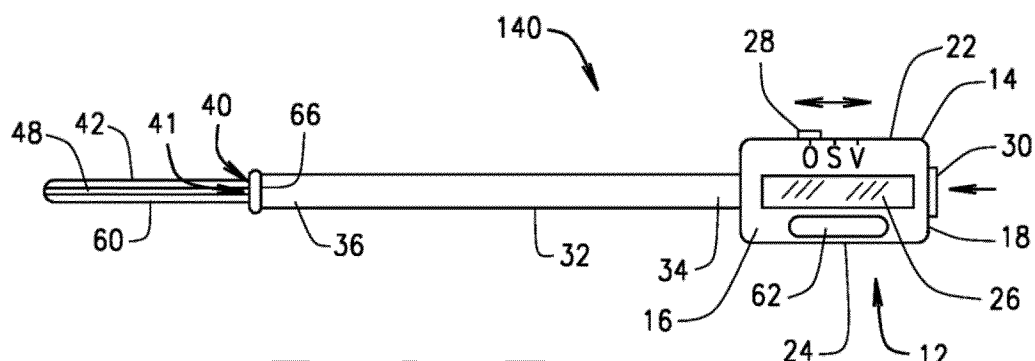
FIG. 7
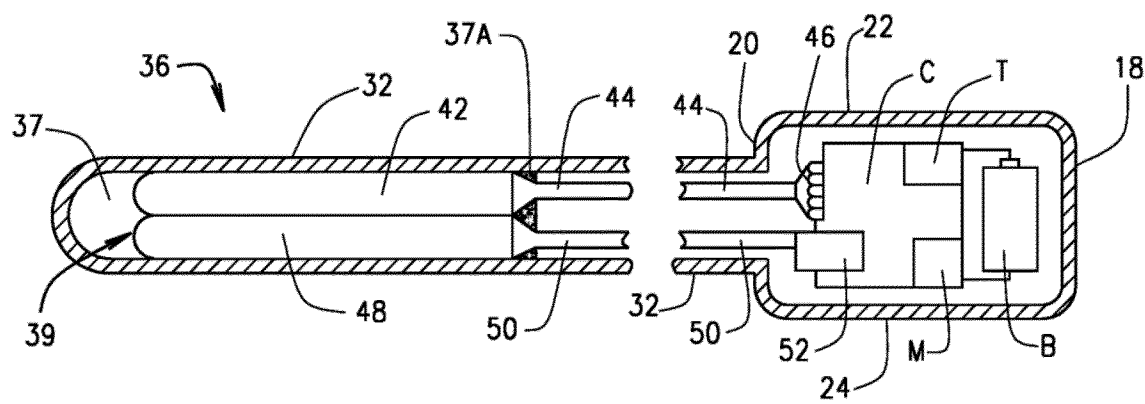
FIG. 8

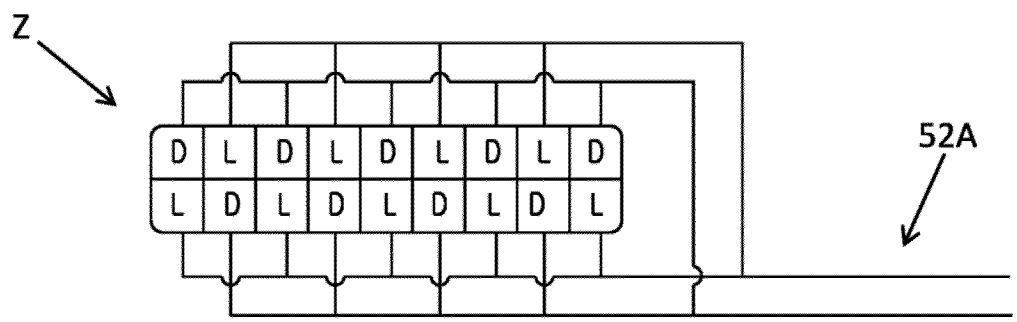
FIG. 9
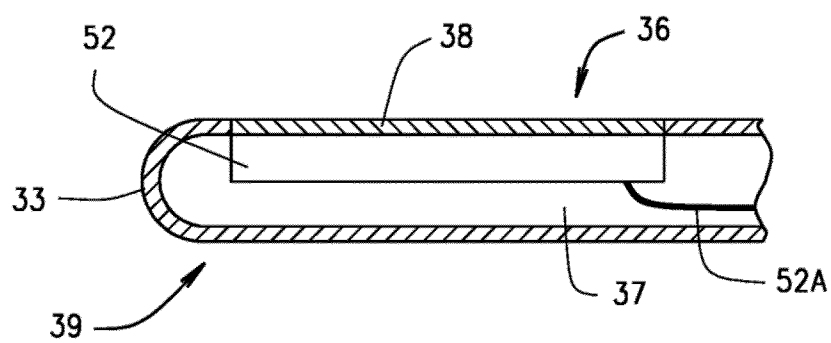
FIG. 10
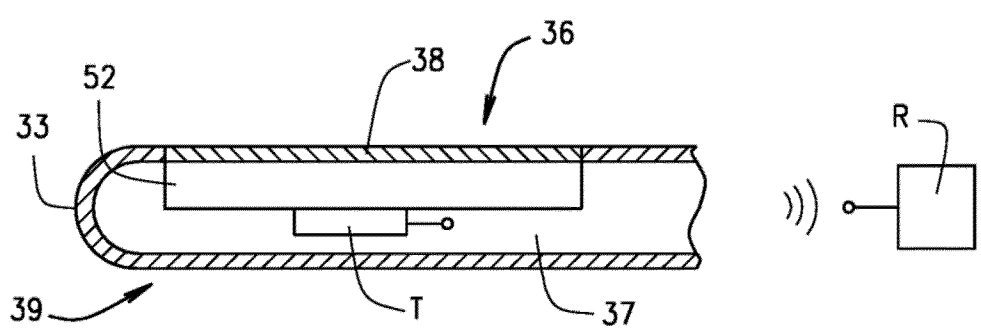
FIG. 11